(12) United States Patent
Goyal et al.

(10) Patent No.: US 12,347,539 B2
(45) Date of Patent: **\*Jul. 1, 2025**

(54) SYSTEM AND METHOD FOR SAFE AND ACCURATE SELF ADMINISTRATION OF MEDICATIONS

(71) Applicant: ILLUMINATE HEALTH, INC., Carmel, IN (US)

(72) Inventors: Varun Goyal, Carmel, IN (US); Kushal C Sacheti, Riverdale, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/514,211

(22) Filed: Nov. 20, 2023

(65) Prior Publication Data

US 2024/0096471 A1  Mar. 21, 2024

Related U.S. Application Data

(63) Continuation of application No. 16/216,056, filed on Dec. 11, 2018, now Pat. No. 11,869,645.

(51) Int. Cl.
| | |
|---|---|
| *G16H 20/10* | (2018.01) |
| *G16H 10/60* | (2018.01) |
| *G16H 40/67* | (2018.01) |

(52) U.S. Cl.
CPC .......... *G16H 20/10* (2018.01); *G16H 10/60* (2018.01); *G16H 40/67* (2018.01)

(58) Field of Classification Search
CPC ........ G16H 20/10; G16H 10/60; G16H 40/67; G16H 70/40
See application file for complete search history.

(56) References Cited

U.S. PATENT DOCUMENTS

| | | | | |
|---|---|---|---|---|
| 7,944,342 | B2* | 5/2011 | Sekura | G16H 20/10 368/10 |
| 2004/0243445 | A1* | 12/2004 | Keene | G16H 20/60 705/2 |
| 2007/0016443 | A1* | 1/2007 | Wachman | G16H 20/10 600/300 |
| 2007/0186923 | A1* | 8/2007 | Poutiatine | G16H 20/13 128/200.14 |
| 2011/0225044 | A1* | 9/2011 | Duffy | G06Q 30/0255 705/14.66 |
| 2014/0058560 | A1* | 2/2014 | Kanagala | A61J 1/00 700/240 |

\* cited by examiner

*Primary Examiner* — Eliza A Lam
(74) *Attorney, Agent, or Firm* — Edlavitch Law PLLC

(57) ABSTRACT

A computer implemented system and method for safe and effective management of self-administration of medication by a user patient, comprising: setting up a user profile on a smart device, receiving medication information and means for pill identification, organization of medications, communication with and involvement of stakeholders such as healthcare providers, family, or loved ones in viewing the timeline of the user patient medication management routine, educating and exposing the user patient to periodic alerts relating to the side effects of certain medications and intra drug interactions, generating an adherence metric consisting of symptom checklist, and contacting the stakeholders when the user patient is not providing an input of their medication intake at the prescribed time intervals, checking metrics and setting goals by and for the user patient on a daily and weekly basis, and means for the user patient to participate in a community of similar users.

20 Claims, 11 Drawing Sheets

SYSTEM AND METHOD FOR SAFE AND ACCURATE SELF ADMINISTRATION OF MEDICATIONS

CROSS-REFERENCE TO RELATED APPLICATIONS

The present application claims the benefit of priority from U.S. Non-Provisional patent application Ser. No. 16/216,056, filed on Dec. 11, 2018, and entitled "SYSTEM AND METHOD FOR SAFE AND ACCURATE SELF ADMINISTRATION OF MEDICATIONS", the entire disclosure of which the application is hereby incorporated herein by reference.

FIELD OF THE INVENTION

The present invention relates generally to self-administration of medications by patients. More particularly, the invention relates to a system and method for enabling a patient to self-administer medications in a safe and accurate manner.

BACKGROUND OF THE INVENTION

A visit to the doctor's office with an ailment generally results in the patient being sent home with one or more medications with specific instructions on self-administering those medications at specified times, in a twenty four hour period. The patient is entrusted with the responsibility of making sure that they follow the medication regimen on their own as the capacity of a physician, family member, or other loved ones to identify and track medication adherence of a patient, is limited. A great majority of chronically ill patients fail to take their medications as prescribed for a variety of reasons including, forgetting to take the medications at the right times and in the right prescribed doses and/or unable to administer the medications themselves due to physical handicaps. The failure to comply with a strict medication intake schedule by these patients results in a steep decline in their health and wellbeing as well as a predisposition to other ailments due to neglect in proper treatment of the current ailment for which the medications were prescribed.

Non-adherence to prescribed medication intake by patients results in increased hospitalization, progression of disease and higher mortality. It is estimated that approximately a third of the United States population and a higher number in third world countries lack the health literacy to accurately follow instructions on taking medications prescribed to them. Several studies have shown that a majority of patients stop taking medications prescribed to them due to unexpected side effects and approximately half of those who stop taking their medications due to side effects, fail to inform their medical professionals that they have stopped taking their prescribed medications. Self-administration of medication requires not just instructions on how to take the prescribed medications, but several support systems to collaboratively function to achieve the desired outcome of a consistent regimented daily schedule for taking prescribed medications. It would be advantageous to have a system and method presented through a user friendly platform that helps patients follow their medication regimens, understand adverse drug interactions, and enable them to interact with their healthcare provider whether they be a physician, nurse practitioner, or pharmacist for counseling when needed, to ensure that the patients are following their medication regimens accurately.

The present invention is a system and method for enabling the safe and accurate self-administration of medications by patients. Patients who use the platform created by the present invention would find it beneficial in helping them comply and adhere to their medication regimen, resulting in the betterment of their health, wellbeing and quality of life. The aim of the system and method of the invention is to educate the user patient on the various medications prescribed to them and provides a means to establish an open communication path between the patient and the various stakeholders such as the patient's physician, or other healthcare provider such as a nurse practitioner, pharmacist, family members, or loved ones so that the patient can seek assistance from these stakeholders if needed, as they follow the medication intake schedule as prescribed.

The primary features of the system and method of the present invention for enabling a safe and accurate intake of prescribed medications by a patient are described in the summary of the invention followed by a more detailed description of the invention through the drawings.

SUMMARY OF THE INVENTION

The present invention is a computer implemented system and method comprising an interactive graphic user interface (GUI) for educating the user patient on the medications prescribed to them and helping them take their medications according to the prescribed regimen with the help of their healthcare providers, family members, or loved ones. The system is comprised of a processor and a set of algorithms to reach the goals of educating the patient user about their prescribed medications and provides the means for the patient to interact with their physician, other healthcare providers, family members, or loved ones to enable them to take their medications according to the prescribed regimen.

The exemplary embodiment of the invention comprises of a system or platform for managing and tracking the entire routine of self-administration of medications by the user patient, data servers with memory for storing the adherence related data, and web servers that run the algorithms/codes to enable interactive and participative medical adherence tracking by the user patient, the medical personal, family members and/or loved ones.

The system, method and platform of the invention further includes codes for personalizing user criteria such as daily routine and medication routine including all the drug related data by the user patient. Further, the platform also involves integrating the social media profiles of the patient user if any and provides an option for the patient user to involve stakeholders such as medical personal, family members, or loved ones to access, view and track the routine of the user patient when they are self-medicating.

The medication management database of the present invention is a thorough and extensive repository of information regarding the type of medications, method of pill identification, method of consumption, and information regarding cross medication interactions which could in some cases have an adverse effect on the patient. The community portal of the platform enables the user patient to interact regularly with their primary care physician, or other medical practitioner they are consulting and may involve personalized chat with their physician, medical practitioner, or a pharmacist, should they have any questions regarding adverse interactions of the medications, or regarding the intake of the medications. Effective communication with their physician, medical practitioner and pharmacist enables the user patient to confidently follow their medication routine without the concern of not effectively complying with the regimen set for them, so that their wellness is safeguarded.

The wellness and medication adherence metrics of the user patient can be viewed and tracked on the user profile page of the platform of the invention which helps the patient adhere to their medication regimen on a systematic basis. The Organization of the medications and pill identification ensures safe and accurate self-administration of the medications which helps the patient follow their medication intake routine, diligently.

The features and advantages of the present invention described in this summary of the invention will become obvious and appreciated by one skilled in the art when viewed in conjunction with the accompanying drawings, detailed description of the invention, and the appended claims.

DETAILED DESCRIPTION OF THE INVENTION

Figure 1:
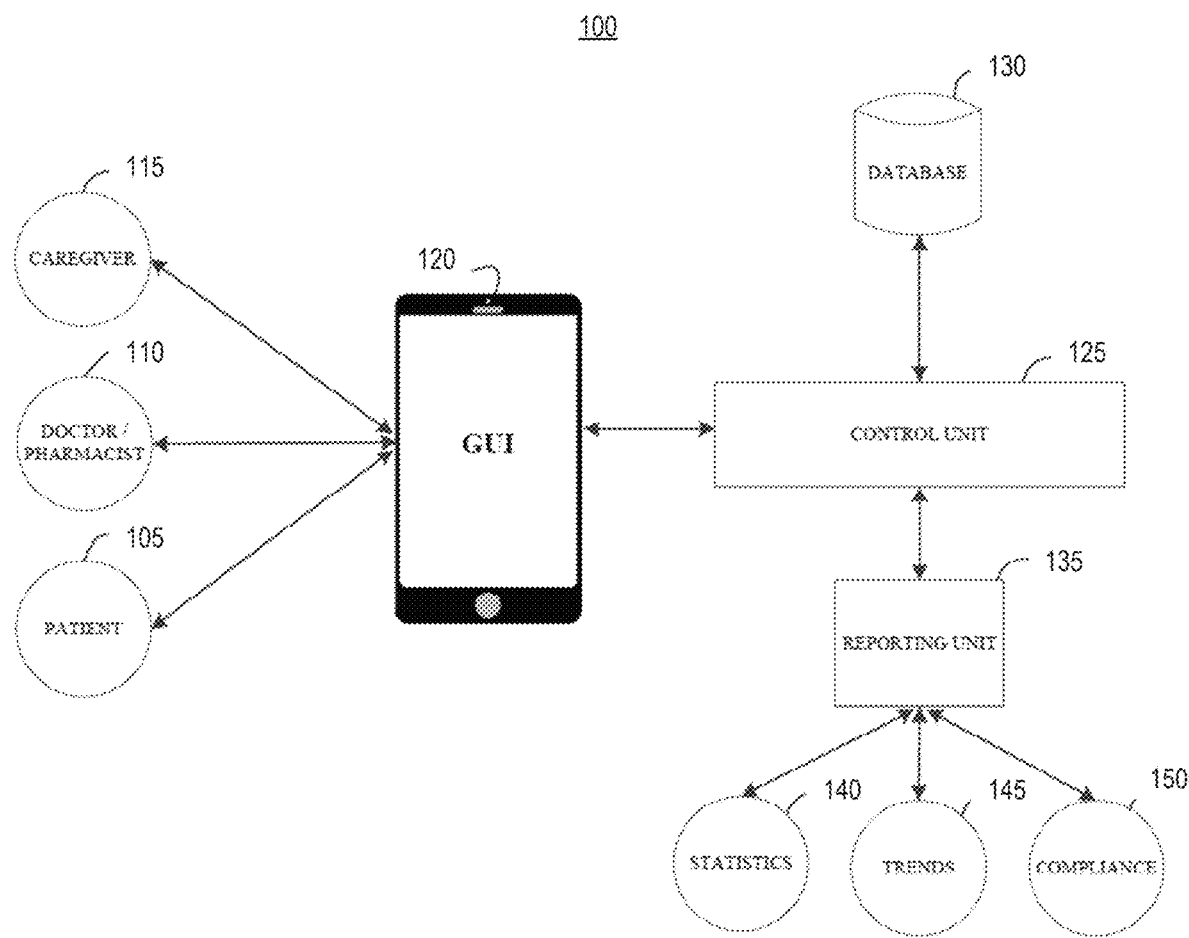
FIG. 1 is a block diagram of the general architecture of the platform used for implementation of one or more of the exemplary embodiments of the present invention.

The present invention is a computer implemented system and method for enabling self-administration of medication in a safe and accurate manner. The platform of the system and its application are structured to enable the user patient to interact with their physician, or other healthcare provider, pharmacist, nurse practitioner as well as their caregivers such as family members, or loved ones collectively referred to hereinafter, as stakeholders. The stakeholders are involved in tracking the medication management of the user patient through the application and platform of the system of the invention. The stakeholders of the user patient are allowed to follow the therapeutic medication routine and regimen of the user patient by accessing the profile of the individual user patient and receiving alerts after communicatively engaging the user patient. Thus the system and method of the invention collectively fosters and entertains multi-way communications and interactions between the user patient and the stakeholders.

In the exemplary embodiments of the present invention, the effective and accurate process and method of self-administration of medication include following a routine for consuming medications for one or more ailments. The process and method of the system not only engages the user patient with following and complying with their medication routine, it also enables a systematic tracking of their medication routine by their physician, other healthcare provider, family members, or loved ones. While the user patient enters the list of medications taken by him/her into the system through his or her profile, the platform of the system helps the user patient to identify the medications based on visual icons of the medication, namely size, shape and characteristics of the pill and thus generates alerts, and educates the user patient on the optimum manner of intake of the medication, potential side effects of the medication on the user, or various intra-medication interactions which could in some instances have adverse effects on them. The various kinds of interactions which could potentially harm the user patient are drug-drug interactions, drug allergy interactions, drug food interactions, drug immunization interactions, and drug disease interactions.

In the exemplary embodiment of the present invention, the application platform takes the information provided by the user patient as an input and connects the control unit to the database where the information is tallied against the existing repository of information in the database, to perform safety checks and alert the user patient on potential side effects of existing medications on the user, or any adverse interactions of the medications with existing allergies or immunizations from the user patient's profile. The user patient gets educated regarding the identification of the medication that is being consumed and is also alerted at periodic intervals regarding intake of medications, thereby helping the user patient to comply with a safe and accurate practice of self-medication. The user patient can rely on the system application database for a variety of information regarding the medications he, or she is taking, like the benefits of the drug, potential side effects that could pose harm and an option to initiate a chat or conversation with their medical practitioner, all of which helps the user patient to organize their medications into a simple daily regimen tailored to the user patient's routine with instructions and precautions provided by the stakeholders. The system thus ensures accuracy and safety in self-medication by the user patient and keeps the stakeholders alerted on the changes or lack of activity on the user patient's profile. The reminders sent as alerts help the user patient identify the medications, learn about the medications, consumption methodologies, and side-effects and thus ensures that the user patient takes their medications on time. The instructions and precautions provided through these alerts and reminders also maximizes the effectiveness of medications and helps the user patient adhere to a safe and accurate routine of self-administration of medication.

In the exemplary embodiment of the invention, the user patient can view and check the metrics on their profile to set goals on a daily and weekly basis to achieve those goals as well as observe and track any possible aberrations in their health. These metrics also help build a community of similar user patients and serves as reference points for interactions between the users of the system.

Referring now to the drawings wherein like numerals represent like components and steps in the several views presented and discussed, and more particularly referring now to FIG. 1 the figure is a block diagram of the general architecture of the system and platform 100 used for implementation of one or more of the exemplary embodiments of the present invention. The system of the present invention comprises of a user patient 105 one or more healthcare providers such as a physician, other medical practitioner, or a pharmacist 110 a caregiver such as a family member or loved one 115, a Graphic User Interface (GUI) 120 which maybe on one of a smart phone, tablet, laptop, or desktop displaying all the relevant information regarding the medications to be self-administered by the user patient 105, and the methods and steps to be taken by the user patient 105 for adherence to the prescribed medication regimen. The system or platform for managing and tracking the entire routine of self-administration of medications, additionally consists of a database 130 which is a repository of information connected to the control unit 125. The control unit 125 accesses the information from the repository of information available from the database 130 which is interactive with the control unit 125 and the information processed at the reporting unit 135 to generate statistics 140, trends 145 and compliance related information 150 for the user patient 105 and any of the stakeholders such as their primary care physician, or other medical practitioner, or pharmacist 110, and caregiver 115. The effective engagement of the user patient 105 through multichannel communications between all these stakeholders in the form of alerts or notifications ensures that the user patient 105 follows the regimen of self-administration of medication in a safe and accurate manner.

Figure 2A:
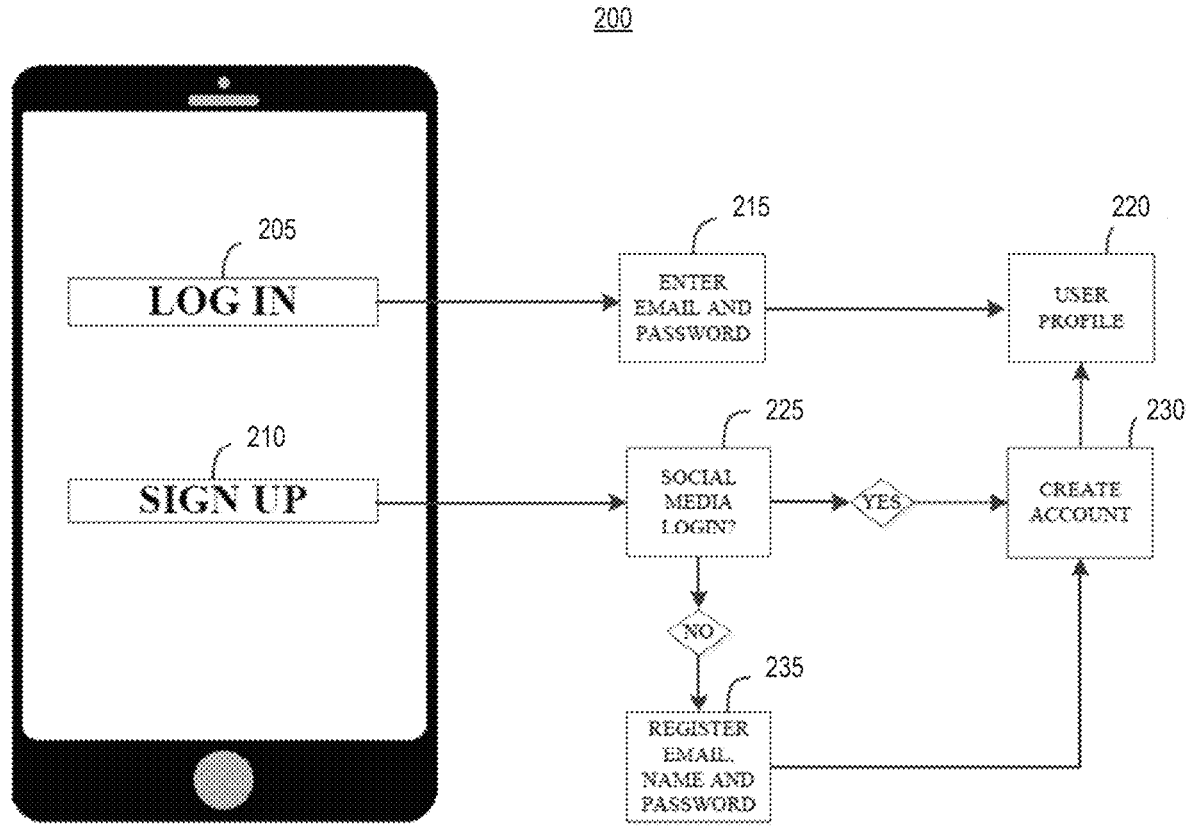
FIG. 2A illustrates a graphic user interface (GUI) on a smart phone for creating a user profile to enable the patient to use the system.

FIG. 2A illustrates a graphic user interface (GUI) on a smart phone for creating a user profile to enable the patient to use the system. The user application interface 200 lets the user patient 105 access the system and method for the safe and accurate self-administration of medication. If the user patient 105 is logging into the system for the first time, he/she is given an option to sign up 210 which involves providing registration details 235 which are then encrypted and saved to the database. The user patient 105 logs in 205 to their user profile 220 by providing their email and password credentials 215 which are encrypted in the web server and would validate the identity of the user patient 105 on the user application interface 200 of the processor operating within a smart device. The user patient 105 also has an option to use his or her social media credentials 225 to access the application interface 200 and view their profile 220. Once the user patient creates the account 230, they are given access to their user profile 220 and requires them to provide information pertaining to medication consumption, medical health records, diseases, vital statistics and other such parameters, to begin the process of tracking their method of medication management and adherence to that regimen. After creating their profile the user patient can edit their profile at any time to add or detract pertinent information and view their achievements on a daily and weekly basis.

A primary care physician, or medical practitioner would have to provide a hospital code for validating their identity which would be encrypted and saved to the database to provide a secure access for them. A user profile is also created by a parent, loved one, or other caregiver and the user patient validates and establishes the relationship.

Figure 2B:
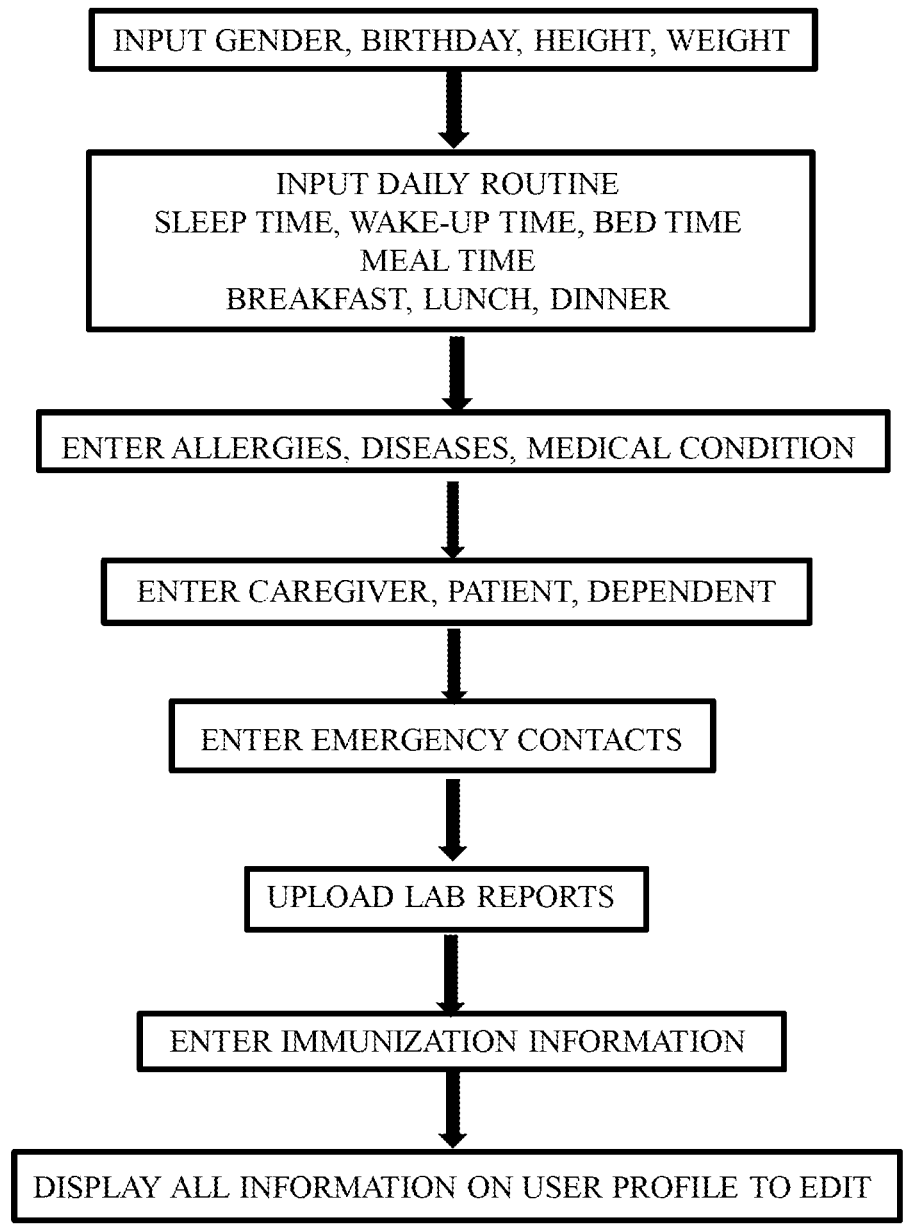
FIG. 2B is a flow chart showing the initial steps involved in the use of the system through the user interface of the invention.

FIG. 2B is a flow chart showing the initial steps involved in the use of the invention through the user interface of the invention after the user patient has created an account. The user patient enters their gender, birthdate and vital statistics such as height and weight, their daily routine such as sleep time, wake-up time, bed time, meal time for breakfast, lunch and dinner, any known allergies and allergies related to medications, diseases and medical conditions they have, enter the names of their caregivers, dependents, emergency contacts, uploads lab reports they receive, immunizations received, and all other pertinent information relating to their medication regimen. The above information is then displayed on the user profile of the patient which can be viewed by their physicians, medical practitioner, and family, or loved ones. All the entered information can be edited by the user patient as new information becomes available, to update their profile.

Figure 3A:
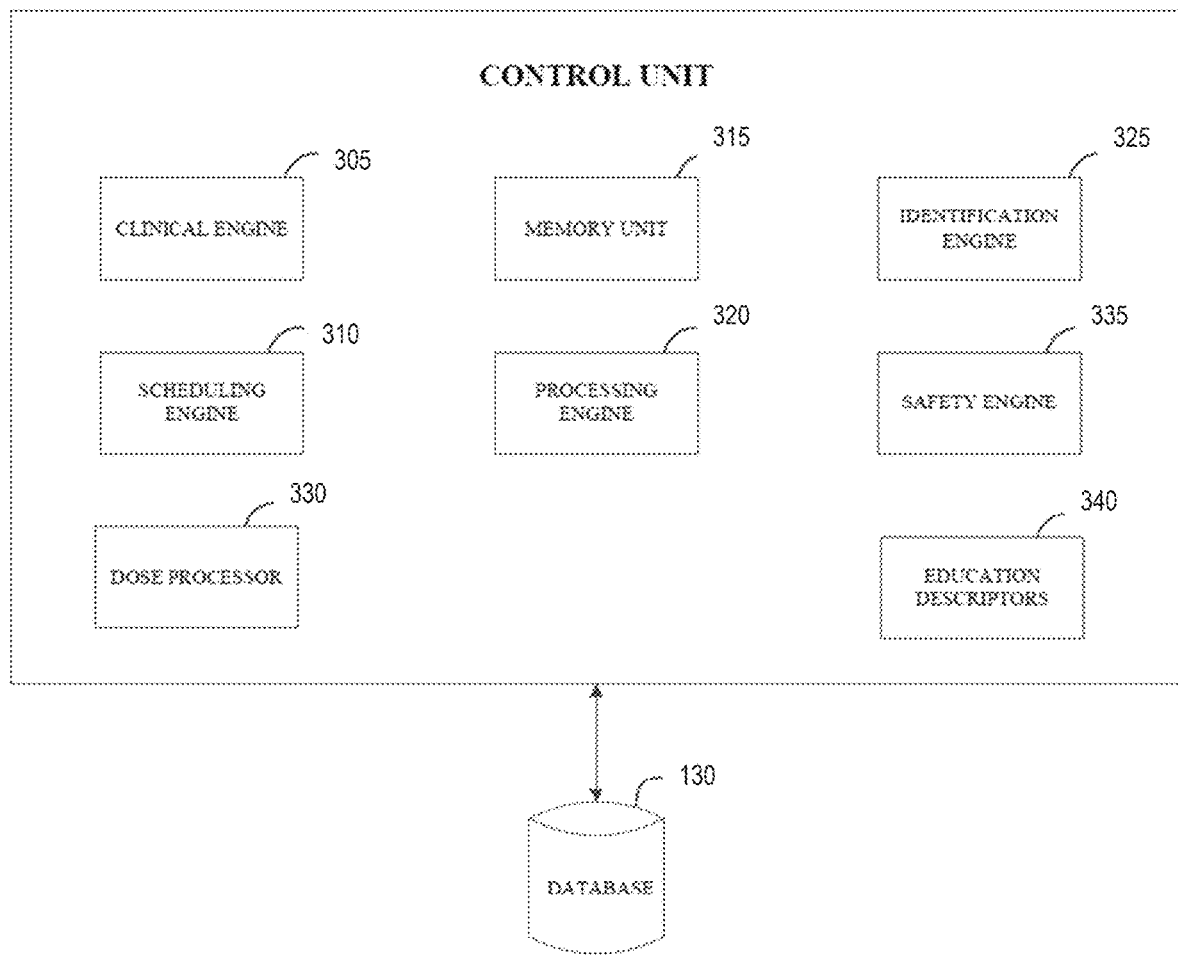
FIG. 3A illustrates the exemplary features of the control unit within the database of the present invention.

FIG. 3A illustrates an exemplary embodiment of the control unit 300 which enables the flow of information in the system application. The control unit 300 comprises a database 130, a clinical engine 305 which processes the user patient's health information and medication regimen, a scheduling engine 310 based on user patient routine which compiles and generates custom medication schedules for the user patient to add to their profile, a memory unit 315 which holds the memory, a processing engine 320 which generates alerts and notifications to the various stakeholders registered with the system and its application, a safety engine 335 which performs safety checks on all types of medication interactions and duplications, an identification engine 325 which identifies the medications from a pool of visual icons of the pills, to connect the pills and other prescribed medications to the associated disease, education descriptors 340 educates the user patient on the medications that are added to the user profile, a dose processor 330 which ensures safe dosing by the user patient.

Figure 3B:
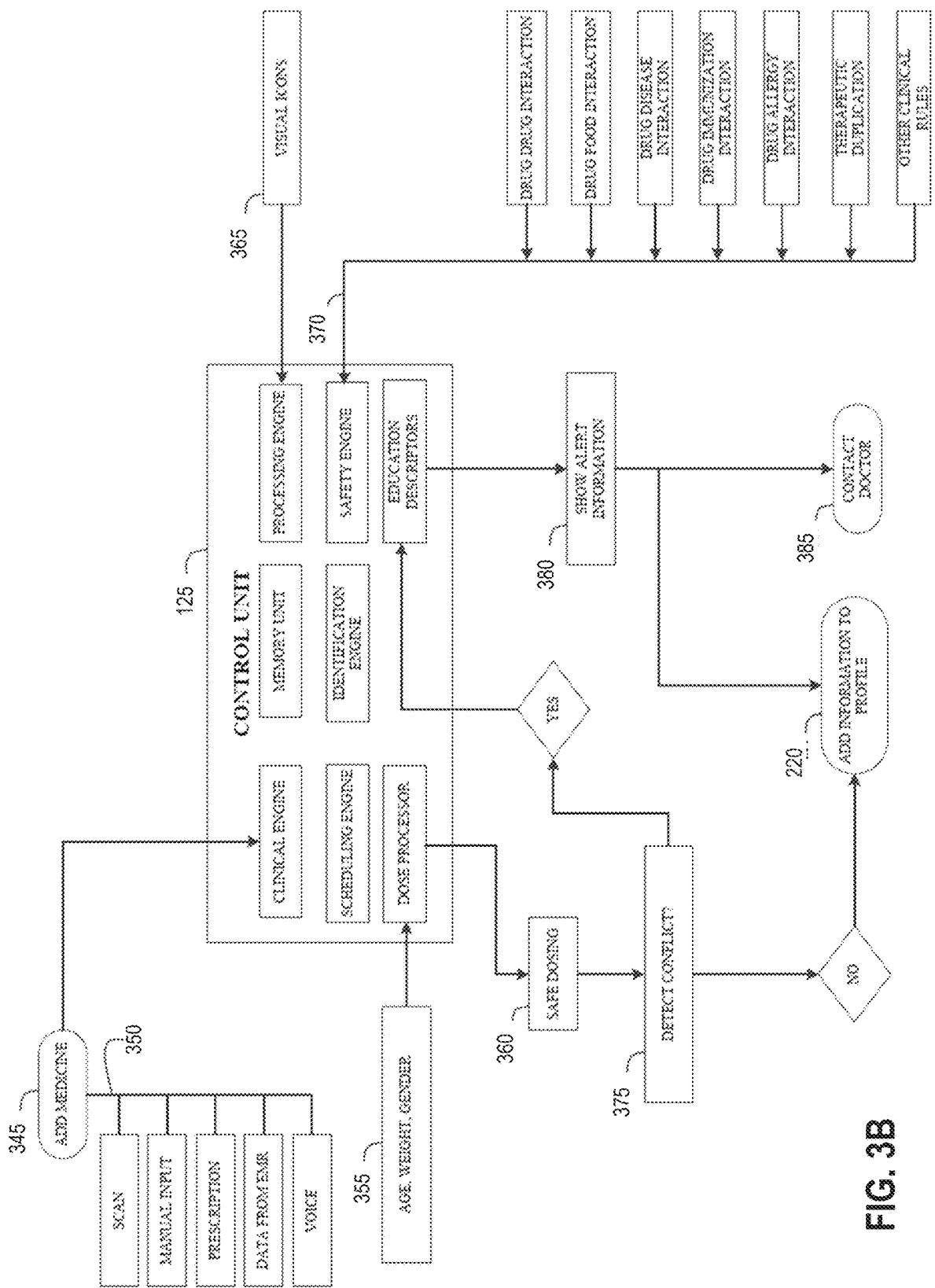
FIG. 3B is a flow chart illustrating the steps involved in implementing the method of the invention through the control unit.

FIG. 3B is a schematic flow chart of the process of adding the information on the medications 345 to the system either by scanning the bar code, providing a manual input, adding information from their prescriptions, or inputting the patient data from their EMR (Electronic Medical Record) 350 after the user patient is granted access to those records. This information is then displayed on the user profile 220 described in FIG. 2A to be viewed by the user on the GUI of their smart phones, tablets, laptops, or desktop computers. All the information can be entered by voice command as well. The information that is provided as an input to the system is processed at the clinical engine 305 of the control unit 125. The medications 345 are provided through a plurality of visual icons 365 on the GUI for the user to identify and the identification is accomplished with the help of a medication identification engine 325 in the control unit 125. The safety engine 335 performs various safety checks to ensure the medication that is being consumed is devoid of any kind of conflicts 375 and the dose processor 330 ensures the user complies with safe dosing 360. The various kinds of conflicts 370 are Drug-Drug Interactions, Drug-Food Interactions, Drug-disease Interactions, Drug-Immunization Interactions, Drug-Allergy Interactions, Therapeutic Duplications, and other Clinical Rules. These safety checks are performed by the Safety engine 335 where the medication that is provided as an input is mapped against the existing information in the database to not display any conflict or life-threatening emergency for the patient user, and the user is alerted in the form of notification generated by the notification processing engine 320 before adding the information 390 for viewing on the graphical user interface (GUI) of the user patient profile. Once a conflict is detected 375, the notification processor engine 320 displays the information to the user patient through the GUI to alert them through the alert information 380 on the possible conflicts 370 and educates them on the options they have. The consumer education descriptors 340 map all the information and adds them to the existing information in the database 130 (see FIG. 3A) of the system. In this way the user patient is educated on the utility value of the medication (s) as well as their side effects. The user patient gets to view these notifications on the user patient interface and gets to snooze 395 those notifications when needed.

The alert information 380 regarding conflicts 375 is also relayed to the physician/doctor 385. If no conflict is detected, the information regarding the medication is customized to lists by the scheduling engine 310 and further utilized to make custom lists, schedule tables and generate alerts either to alert the stakeholders of the system application or add to the user profile. The alerts provided to the user or stakeholders could be in the form of emails, instant messages, chats, or other relevant formats. In general, the user patient, or the patient support team may be requested by the alert to respond with an update. For example, if the medication has been taken, a user patient may enter this fact, optionally in response to the alert, or independently of the alert. Such a data entry may then neutralize or otherwise change the status of the current alert and may be used to manually or automatically reset the reminders settings. If the medication, and or medications have not been taken, the user patient may enter this fact optionally in response to the alert, or independently of the alert. In such a case, the scheduling engine may recycle or re-activate the alert. The alert may be sent immediately or later (e.g. time defined by patient or automatically set by the application) to the user patient and to the stakeholders. Other steps or combination of steps may also be used. The system of the invention also provides a doctor portal for accessing information on their medications and requesting a refill or renewal request from the healthcare provider or pharmacist.

For the effective and efficient self-administration of medication and medication management, the user interface of the system provides a view of the schedule, calendar view, my medications and other statistical features. Visual icons of the medications are also displayed to enable the user patient to understand and learn about the medications they are taking before adding them to their profile. The user patient could also add medicines as needed to learn further about taking the medication or consulting a practitioner for further questions to effectively comply with the routine.

Figure 3C:
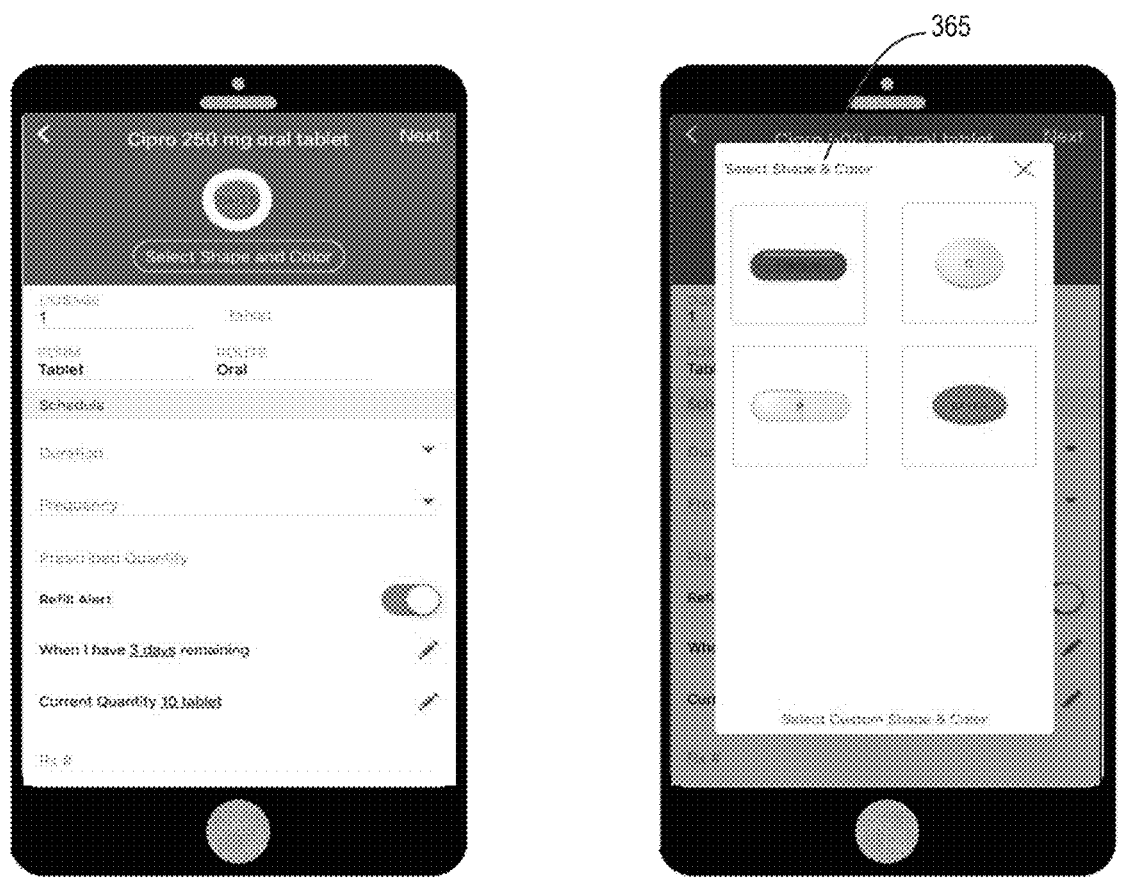
FIG. 3C shows perspective views of the graphic user interface on a smart device such as a smart phone, more particularly of screen shots of a prescribed medication tablet on one screen and images of the tablet size and shape on the second screen.

FIG. 3C shows perspective views of the graphic user interface on a smart device such as a smart phone, more particularly of screen shots of a prescribed medication tablet on one screen and images of the tablet size and shape on the second screen. The user interface facilitates pill identification with the help of a visual icons 365 and informs the user patient of the last medicine taken and what is next on the list. These visual icons 365 help the user to identify and register the pill to remember and recollect the instructions better. The visual icons 365 and options provided help the user to identify whether the medication has been taken and the consumer education information that goes along with it, lets the user customize their profile according to the criteria of medication intake, dosage and frequency. The organized medication with simplified instructions and precautions with iconized visual of the visual identity of the pill and the disease for which it is being taken for, enables accuracy and safety during the self-administration routine, on a daily basis. The scheduling engine allows the user to edit and amend the dietary and medication schedule. The user interface display of my medications lets the user view information regarding the medications, change in medications, amend the medications added to the profile and opt to receive, or snooze the alerts and notifications.

Figure 3D:
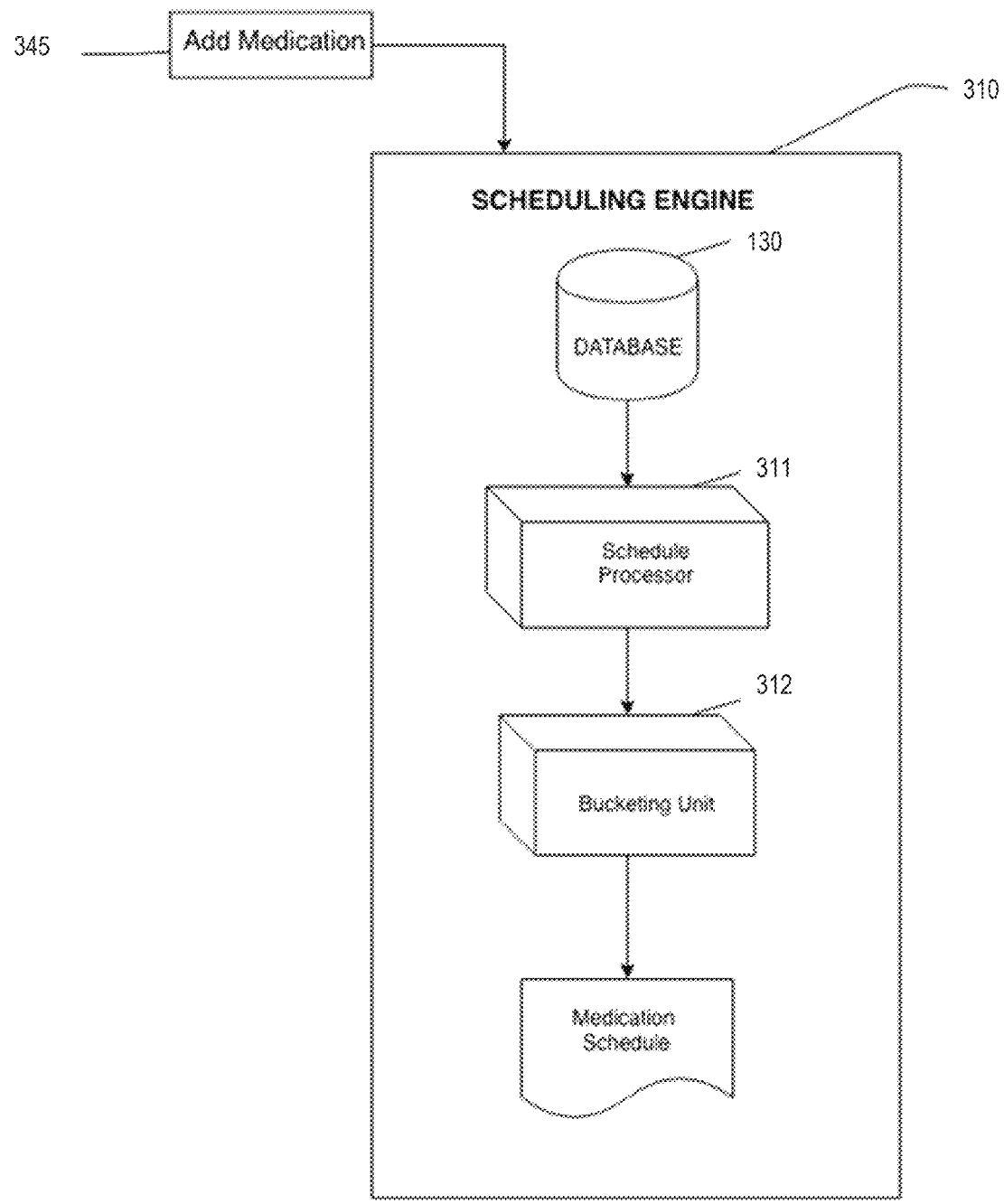
FIG. 3D is a flow chart showing the components of the scheduling engine within the control unit that functions to determine a medication schedule for the patient.

FIG. 3D is a flow chart showing the components of the scheduling engine 310 within the control unit 300 and the generation of a medication schedule for the patient. The scheduling engine 310 has two components, a schedule processor 311 and a bucketing unit 312. The schedule processor 311 utilizes the routine information of the patient from the database 130 including timing of when a patient sleeps, wakes up and has a meal. The schedule processor 311 also utilizes clinical rules which are stored in the database 130 along with medication information to identify the best time of day when the patient should take the recommended medication 345. The bucketing unit 312 uses the time of day to slot the medication into the times when the patient is already scheduled to take another medication, or creates a new schedule time for the new medication. In this manner, the daily medication schedule for the patient is created with an aim to maximize patient wellness and minimize unintended side effects. The scheduling engine 310 uses a set of algorithms aimed at detecting medication properties and patient routine to schedule the best time of day for taking medication, in hopes of decreasing side effects and increasing wellness. That way the patient or family member does not have to worry about the confusing task of when the patient should to take each medication. In this manner, a medication schedule is created for the patient for the easy and accurate self-administration of medications by the patient.

Figure 3E:
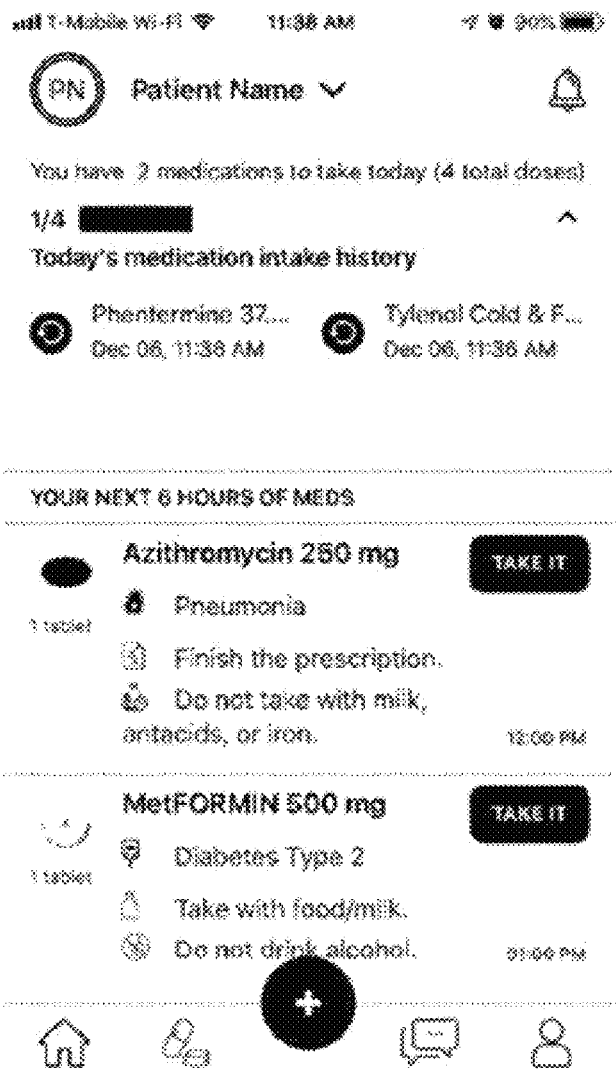
FIG. 3E is a screen shot image on the graphic user interphase of a smart device illustrating an example of medication intake instructions provided and viewed by the patient using the exemplary embodiment of the invention.

FIG. 3E is a screen shot image on the graphic user interphase of a smart device illustrating an example of medication intake instructions provided and viewed by the patient using the exemplary embodiment of the invention. The patient name is displayed to view the identity of the user of the system application along with the information relating to the medications taken, with instructions on how to take them, medication interactions, and pertinent side effects. For example, in the case of some medications, the user patient could experience drowsiness, nausea, or headache which could cause confusion and fear in continuing to take the medication on a day to day basis. The system provides the means for the patient to alert the physician, or other caregiver on these symptoms and seek advice on changing medications if needed. Such a display makes it an effective way of managing medications prescribed to the patient and viewing the adherence related data anytime.

Figure 4:
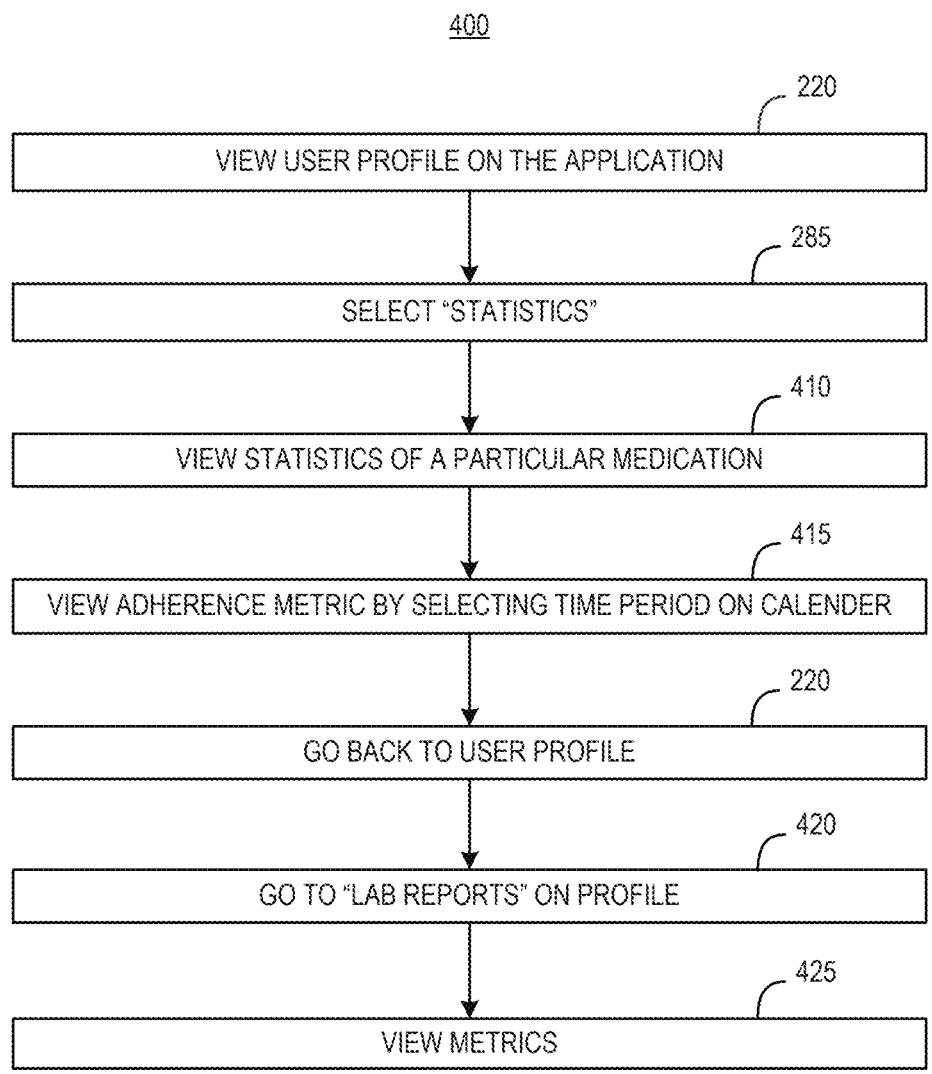
FIG. 4 is a flow chart depicting the steps involved in the user patient accessing their statistics and adherence metrics with reference to their medication intake and viewing their laboratory profile.

FIG. 4 is a flow chart depicting the steps involved in the user patient accessing their statistics and adherence metrics with reference to their medication intake and viewing their laboratory profile. The generation and display of statistics enables the user patient to view metrics to compare and analyze their performance in medication management and understand the level of their adherence so that they can identify concerns and address them for accurate adherence to the regimen. This feature also engages the user in understanding their own regimen to seek help or clarifications and communicate, or reach out to the practitioner or caregiver, and the metrics let the user track the adherence related data and hence effectively and accurately comply with the medication management schedule and routine. The metrics are displayed in the form of histogram or line graph or any other pictorial representation which lets the user track the analytics for any purpose. The user patient can track their achievement trophies and rewards gained which helps them stay engaged and motivated with the routine of self-administration of medication.

Figure 5:
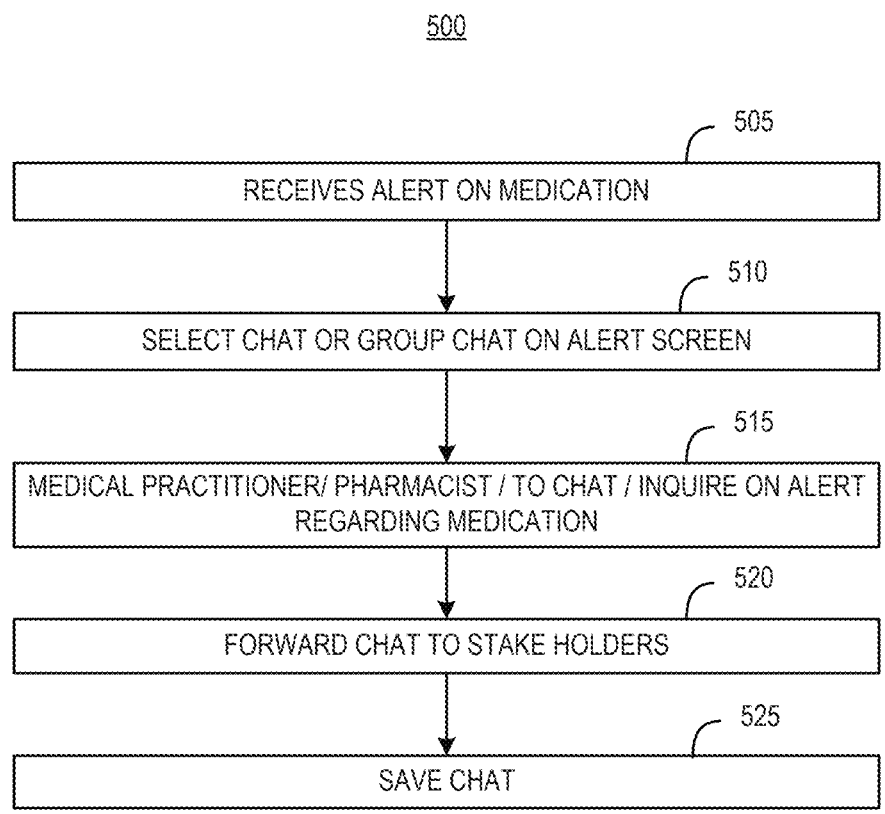
FIG. 5 is a flow chart depicting the patient receiving an alert on a medication and following up with a chat session with their medical care provider for advise on the alert and forwarding the chat contents to other stakeholders and saving the chat session.

The user interface also displays a chat feature which lets the user-reach out to a medical practitioner pharmacist, or a loved one registered on the system_application as a stakeholder regarding the user patient's concerns and seeking clarifications in reference to the self-administration of medication and accurate management of the routine. FIG. 5 is a flow chart depicting the patient receiving an alert on a medication and following up with a chat session with their medical care provider for advice on the alert and forwarding the chat contents to other stakeholders, and saving the chat session.

Figure 6:
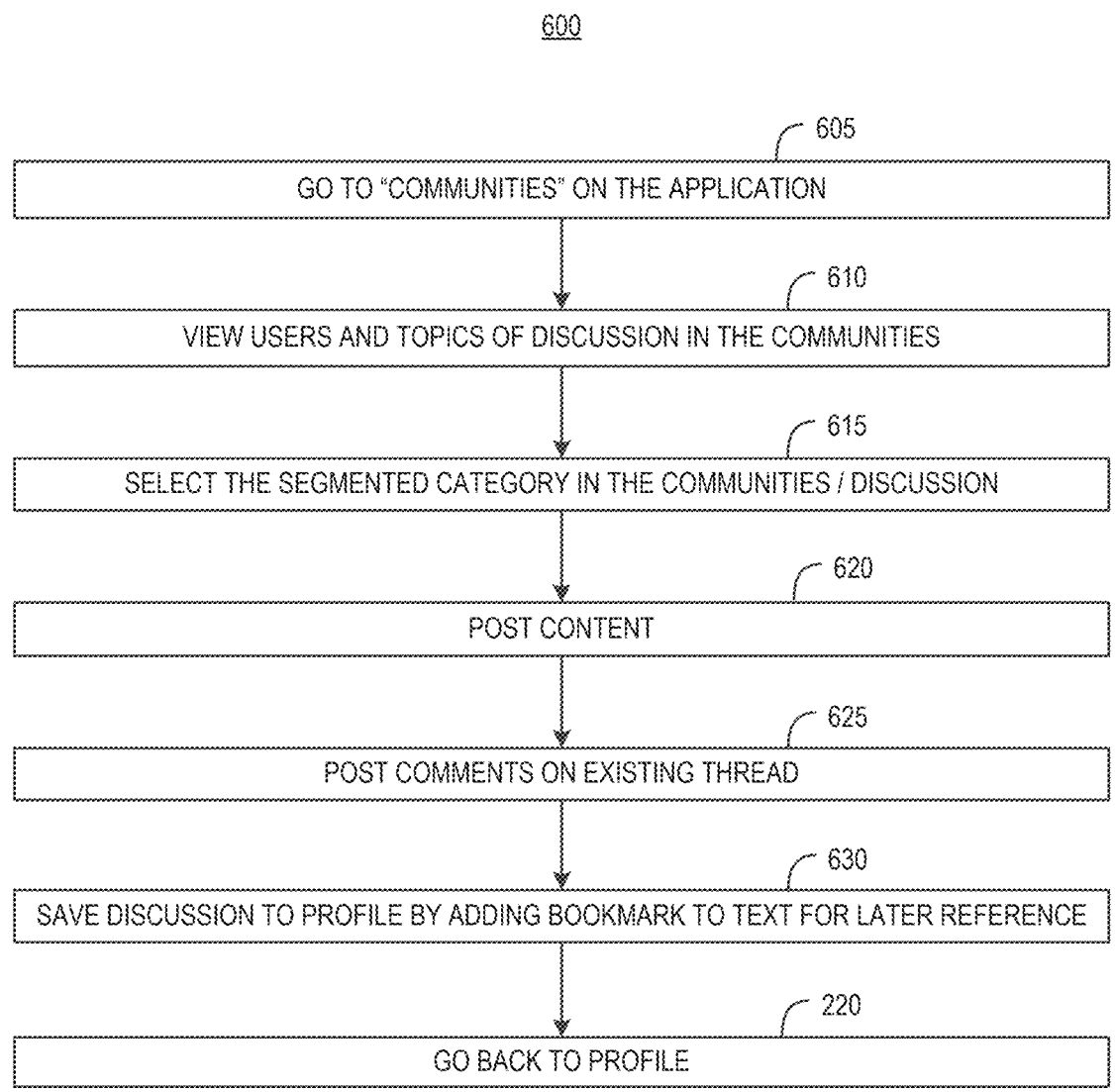
FIG. 6 is a flow chart of the user patient's activities with other members in the community who use the system and method provided by the platform of the invention.

The platform of the system has a feature for community participation and interaction which lets the user patient correspond, interact and communicate with others who are adhering to a similar medication regimen. The communities feature also lets the user patient engage and interact with people of related interests, or participate in an activity thereby effectively adhering to the self-administration of medication and the schedule. FIG. 6 is a flow chart of the user patient's activities with other members in the community who use the system and method provided by the platform. Through this feature, the user patient can access information on topics of interest in the community of users, select the segment and category in the communities discussion thread and participate posting and receiving constant on these threads. Through this feature, the user patient can also save the discussions of interest to them and book mark them for later reference.

While the present invention has thus been described through its preferred embodiments and related figures, it is to be understood that the embodiments of the present invention as described herein do not limit any application or scope of the invention and that the invention can be carried out and practiced in various ways and implemented in embodiments other than the ones outlined and described above. It should be understood and obvious to one skilled in the art that alternatives, modifications, and variations of the embodiments of the present invention may be construed as being within the spirit and scope of the appended claims.

The invention claimed is:

1. A system, comprising:
an alerting graphical user interface (GUI); and
a computing system, configured to:
  generate or update a patient profile for a user patient, which comprises a medication routine for the user patient;
  identify an instance where the user patient changes the patient profile;
  generate a first alert according to the identification of the instance where the user patient changes the patient profile; and
  upon generation of the first alert, communicate, via the alerting GUI, the first alert to additional users that are identified as other stakeholders of the patient profile, and
  wherein a first GUI is configured to receive an input that the user patient is experiencing certain side effects from the medication routine,
  wherein the computing system is further configured to activate a second alert based on the receiving of the input that the user patient is experiencing certain side effects from the medication routine,
  wherein the upon generation of the second alert, the computing system is further configured to communicate, via a second GUI, the second alert to the additional users that are identified as the other stakeholders of the patient profile,
  wherein the first GUI displays a chat feature configured to facilitate the user patient reaching out to the additional users regarding concerns of the user patient related to the second alert and seek clarifications in reference to self-administration of medication and accurate management of the routine as well as seek advice on changing medications,
  wherein the computing system is further configured to store a chat session provided by the chat feature,
  wherein the first GUI is further configured to provide access to the stored chat session,
  wherein the communication of the second alert via the second GUI occurs through the chat feature, and
  wherein the chat feature is displayed at a lower portion of the first GUI when the first GUI is displayed on a smart device.

2. The system of claim 1, wherein the computing system is further configured to:
identify an occurrence of the user patient not interacting with the patient profile for a preselected duration of time;
generate a third alert according to the identification of the occurrence of the user patient not interacting with the patient profile for the preselected duration of time; and
upon generation of the third alert, communicate, via the alerting GUI or a third GUI, the third alert to the additional users that are identified as the other stakeholders of the patient profile.

3. The system of claim 2, further comprising a medication input UI, configured to receive an input of a plurality of medications from the user patient.

4. The system of claim 3,
wherein the medication input UI is a separate GUI, and
wherein for selecting the input of the plurality of medications, the system provides identifications of medications through visual icons of the medications, including size, shape and other characteristics of the medications.

5. The system of claim 3,
wherein the medication input UI is a separate GUI, and
wherein the medication input UI is further configured to display, via a first screen, a screen shot of one of the plurality of medications.

6. The system of claim 5, wherein the medication input UI is further configured display, via a second screen, an icon showing a shape, size, and color of the medication.

7. The system of claim 6, wherein the computing system is further configured to:
receive, via the medication input UI, an input on the shape, size, and color of the plurality of medications; and
further generate the medication routine according to the input on the shape, size, and color of the plurality of medications.

8. The system of claim 3,
wherein the medication input UI is a separate GUI, and wherein the medication input UI displays the chat feature configured to facilitate the user patient directly communicating with the additional users.

9. The system of claim 3, wherein the alerting GUI, the medication input UI, or another UI is further configured to provide access to the stored chat session.

10. The system of claim 3, wherein the generation or updating of the patient profile for the user patient is at least partially based on a mapping the input of the plurality of medications with a pre-stored set of instructions and information of the plurality of medications.

11. The system of claim 1, wherein the computing system is further configured to record patient interactions with the patient profile as adherence data.

12. The system of claim 11, wherein the computing system is further configured to generate and display adherence information derived from the adherence data.

13. The system of claim 12, wherein the adherence information provide levels of adherence to the routine by the user patient.

14. A computer-implemented method, comprising:
generating a medication routine for a user patient;
identifying an instance where the user patient changes the generated routine through a user interface;
generating a first alert according to the identification of the instance where the user patient changes the routine; and
upon generation of the first alert, communicating, via an alerting graphical user interface (GUI), the first alert to additional users that are identified as other stakeholders of the routine, and
wherein a first GUI is configured to receive an input that the user patient is experiencing certain side effects from the medication routine, and
wherein the method further comprises:
activating a second alert based on the receiving of the input that the user patient is experiencing certain side effects from the medication routine;
upon generation of the second alert, communicating, via a second GUI, the second alert to the additional users that are identified as the other stakeholders of a patient profile for the user patient;
the first GUI displaying a chat feature configured to facilitate the user patient reaching out to the additional users regarding concerns of the user patient related to the second alert and seek clarifications in reference to self-administration of medication and accurate management of the routine as well as seek advice on changing medications;
storing a chat session provided by the chat feature; and
the first GUI providing access to the stored chat session,
wherein the communication of the second alert via the second GUI occurs through the chat feature, and
wherein the chat feature is displayed at a lower portion of the first GUI when the first GUI is displayed on a smart device.

15. The method of claim 14, further comprising:
identifying an occurrence of the user patient not interacting with the routine for a preselected duration of time;
generating a third alert according to the identification of the occurrence of the user patient not interacting with the routine for the preselected duration of time; and
upon generation of the third alert, communicating, via the alerting GUI or a third GUI, the third alert to the additional users that are identified as the other stakeholders of the routine.

16. The method of claim 15, further comprising a medication input UI receiving an input of a plurality of medications from the user patient.

17. The method of claim 16, further comprising the medication input UI providing identifications of medications through visual icons of the medications, including size, shape and other characteristics of the medications.

18. The method of claim 17, further comprising the medication input UI displaying, via a first screen, a screen shot of one of the plurality of medications.

19. The method of claim 18, further comprising the medication input UI displaying, via a second screen, an icon showing a shape, size, and color of the medication.

20. The method of claim 19, further comprising:
receiving, via the medication input UI, an input on the shape, size, and color of the plurality of medications; and
further generating the medication routine according to the input on the shape, size, and color of the plurality of medications.

* * * * *